United States Patent [19]
Dinger et al.

[11] Patent Number: 5,525,297
[45] Date of Patent: Jun. 11, 1996

[54] MEASUREMENT ARRANGEMENT FOR MULTIPLE ZONE REMOVABLE SENSORS

[75] Inventors: Rudolf Dinger, St-Aubin; Eric Hoffmann, Ipsach, both of Switzerland

[73] Assignee: Asulab S.A., Bienne, Switzerland

[21] Appl. No.: 304,859

[22] Filed: Sep. 13, 1994

[30] Foreign Application Priority Data

Sep. 21, 1993 [FR] France .................................. 93 11316

[51] Int. Cl.⁶ ............................ B32B 31/18; G01N 33/48
[52] U.S. Cl. .............................. 422/63; 422/66; 156/526; 156/579
[58] Field of Search ................................. 422/63, 66, 58, 422/61, 82.01; 156/523, 526, 579; 436/95

[56] References Cited

U.S. PATENT DOCUMENTS

| | | | |
|---|---|---|---|
| 2,732,964 | 1/1956 | Neer | 156/523 |
| 4,008,119 | 2/1977 | Hermann | 156/579 |
| 4,116,747 | 9/1978 | Hamisch | 156/579 |
| 4,253,905 | 3/1981 | Regan | 156/579 |
| 4,301,729 | 11/1981 | Fujita | 156/579 |

FOREIGN PATENT DOCUMENTS

| | | |
|---|---|---|
| 9010861 | 9/1990 | WIPO . |
| 9214836 | 9/1992 | WIPO . |
| 9221961 | 12/1992 | WIPO . |

*Primary Examiner*—Lyle A. Alexander
*Attorney, Agent, or Firm*—Griffin, Butler, Whisenhunt & Kurtossy

[57] ABSTRACT

A measurement arrangement, in particular for measuring the proportion of glucose in the blood, which is intended to be associated with a removable sensor including a plurality of single use active zones includes a cutting arrangement (44, 64, 66, 68, 70) serving to cut off the removable sensor (52) introduced into the measurement arrangement. The cutting arrangement comprises a lever (44), a crank (66) and a blade (70) fixed on the lever.

20 Claims, 4 Drawing Sheets

MEASUREMENT ARRANGEMENT FOR MULTIPLE ZONE REMOVABLE SENSORS

FIELD OF THE INVENTION

The present invention concerns a measurement arrangement intended to be associated with a removable sensor including a plurality of single use active zones, such removable sensor being hereinafter referred to as multiple zone sensor.

More specifically, the present invention concerns a cutting arrangement comprised in such measurement arrangements. Such cutting arrangement serves to cut off an active zone following use thereof to effect a measurement, specifically a measurement of the electrochemical type, of a multiple zone sensor introduced into the measurement arrangement so as to separate the portion of the multiple zone sensor, including such used active zone, from the remainder of the multiple zone sensor.

BACKGROUND OF THE INVENTION

On FIGS. 1 and 2 is shown an electrochemical measurement arrangement such as described in the patent application FR 92 01331.

On FIG. 1 is shown partially and in perspective an exploded view of the multiple zone sensor including an insulating substrate 2 on the surface of which are provided two electrodes 4 and 6 serving to conduct an electrical measurement current. On such electrodes 4 and 6 is provided a coating 8 also insulating.

The coating 8 includes a first series of openings 10a, 10b, 10c at least partially superposed onto the first electrode 4 and a second series of openings 12a, 12b, 12c at least partially superposed onto the second electrode 6. At one end 13 of coating 8 is provided at least one opening 14 serving to free an electrical contact surface on each of the two electrodes 4 and 6.

It will be noted that electrodes 4 and 6 are electrically insulated from one another and that the first series of openings 10a, 10b, 10c is not superposed onto the second electrode 6. Likewise, the second series of openings 12a, 12b, 12c is not superposed onto the first electrode 4. Each pair of corresponding openings respectively 10a and 12a, 10b and 12b, 10c and 12c, defines an active zone of the multiple zone sensor.

The electrochemical functioning of such a multiple zone sensor is substantially identical to that of a single zone sensor such as described for example in the patent application Wo 92/14836.

The substance to be analyzed, for example blood in a possible application for the measurement of glucose therein, is brought into one of the active zones of the multiple zone sensor. To effect a valid electrochemical measurement it is necessary that only one of the active zones of the multiple zone sensor be covered by the substance to be analyzed, the remaining active zones having necessarily to remain unused.

On FIG. 2 is shown an electrochemical measurement arrangement designated by the general reference 20 intended to receive a removable multiple zone sensor of the type of that described on FIG. 1.

The electrochemical measurement arrangement 20 comprises a case 22 in the interior of which is provided electronic measurement means 24. Additionally, such electrochemical measurement arrangement 20 comprises an advancing arrangement 26 serving to displace the multiple zone sensor 28 introduced into the interior of case 22.

In order to cut off an active zone, following use thereof in order to effect an electrochemical measurement, of the multiple zone sensor 28 so as to separate the portion of such multiple zone sensor 28, including such used active zone, from the remainder of the latter, there is provided a cutting arrangement 30.

The cutting arrangement 30 comprises a push-piece 32 and a blade 34 fixed to such push-piece 32. The cutting arrangement 30 is arranged in a manner such that push-piece 32 is adapted to effect a displacement, in a direction transversal to the multiple zone sensor 28, sufficiently great to permit blade 34 to traverse completely such multiple zone sensor 28.

The cutting arrangement 30 described hereinbefore exhibits various drawbacks. Initially, it is necessary to exert a relatively high pressure on push-piece 32 in order to cut off the multiple zone sensor 28. Secondly, it is very difficult to gage manually the pressure exerted on the push-piece 32, given the heavy pressure necessary for cutting off the multiple sensor 28. Accordingly, the cut-off portion absorbs at the end of the cutting travel a high strain energy in a very short time lapse which generates a relaxation phenomenon propelling the cut-off portion relatively far from the case 22. This latter drawback represents a particular disadvantage given that the product to be analyzed risks spreading at least partially beyond the active zone in which it has been placed. Additionally, the localization of the cut-off portion can be rendered difficult given the indeterminate direction of propulsion of the cut-off portion. When the product to be analyzed is a product dangerous for man or his environment, this latter drawback renders utilization of the electrochemical measurement arrangement described hereinbefore hardly to be recommended.

A purpose of the present invention is to overcome the drawbacks mentioned hereinabove in providing a measurement arrangement including a cutting arrangement permitting a control of the advance of the blade in a manner to assure a slight displacement of the cut-off portion relative to the measurement arrangement.

SUMMARY OF THE INVENTION

To such effect, the present invention concerns a measurement arrangement, intended to be associated with a multiple zone removable sensor comprising a cutting arrangement for said multiple zone removable sensor and characterized in that said cutting arrangement includes a lever, a crank and a blade, said lever effecting a rotation around a first axle whenever it is actuated, said crank being mechanically coupled to said lever and adapted to undergo a rotation around a second axle different from said first axle and fixed to said lever, said blade being mechanically coupled to said crank and arranged in the interior of a guide defining a predetermined path for such blade whenever said lever is actuated, said measurement arrangement being arranged in a manner such that said blade enables the cutting of said multiple zone removable sensor placed within said measurement arrangemment whenever said lever is actuated between an initial cutting position and a final cutting position.

Another purpose of the invention is to furnish a cutting arrangement arranged in a manner such that the cutting force exerted by the blade on the multiple zone removable sensor is greater than the force exerted by the user in order to cut off such multiple zones removable sensor placed within the measurement arrangement.

To this effect and according to the specific characteristics of the measurement arrangement according to the present invention, the first and second axles are parallel and the lever exhibits a dimension greater than the distance provided between such first and second axles in a plane perpendicular to said first and second axles.

The measurement arrangement according to the invention enables transforming a circular motion of the lever into a substantially rectilinear motion of the blade Accordingly, it is possible better to control the force exerted on the blade. Next, there results from the specific characteristics mentioned hereinbefore that the cutting force exerted by the blade on the multiple zone sensor is greater than the force exerted by a user substantially at the free end of the lever. Thus, the cutting of the multiple zone sensor and the control of the speed of advance of the blade in the latter are facilitated.

Other characteristics and advantages of the invention will be described hereinafter with the help of the following description made having reference to the attached drawings, given by way of non-limiting examples.

DESCRIPTION OF THE PREFERRED EMBODIMENTS

With the help of FIGS. 3 to 5, there will be described hereinafter an embodiment of a measurement arrangement according to the invention.

Figure 1:
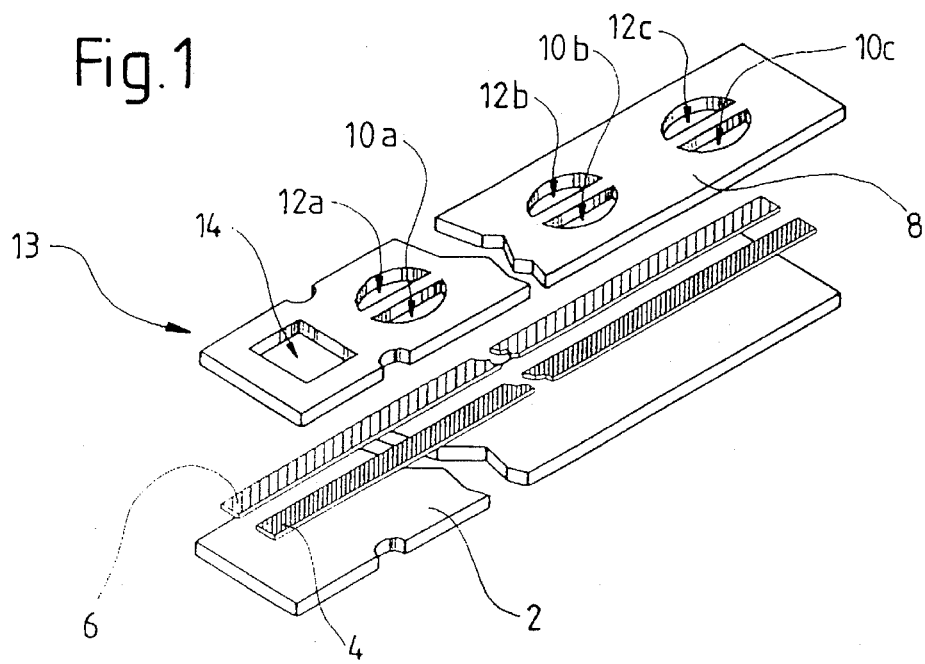
FIG. 1, already described, shows in perspective an exploded view of a removable multiple zone sensor.
Figure 2:
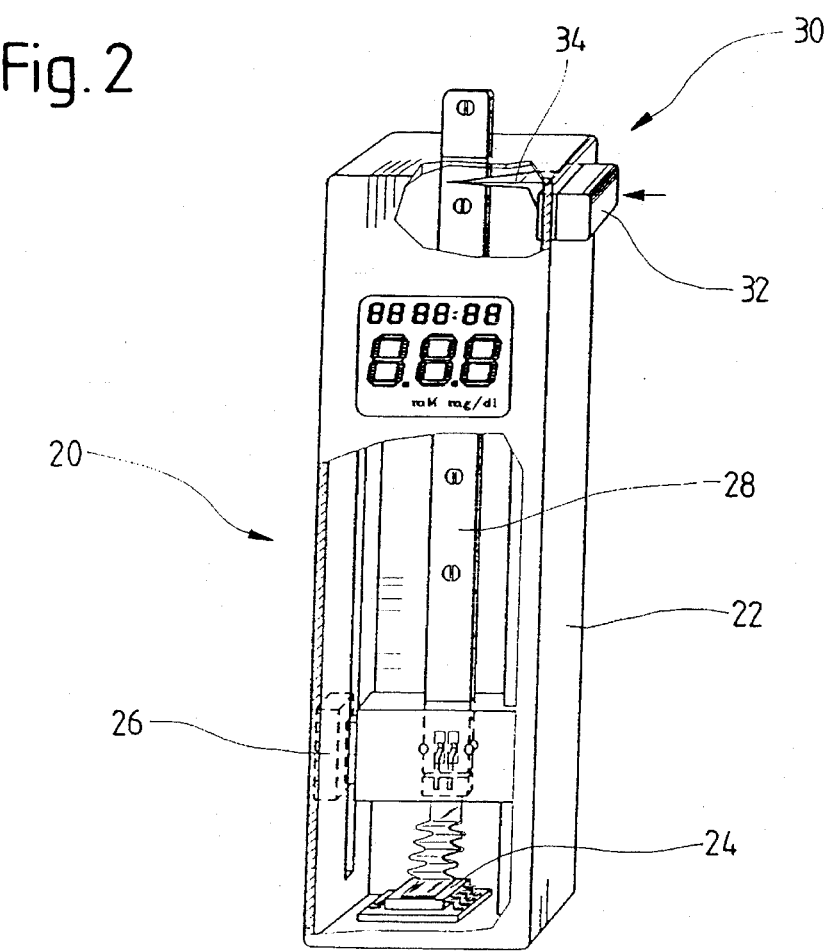
FIG. 2, already described, shows schematically a measurement arrangement associated with the multiple zone removable sensor shown on FIG. 1.
Figure 3:
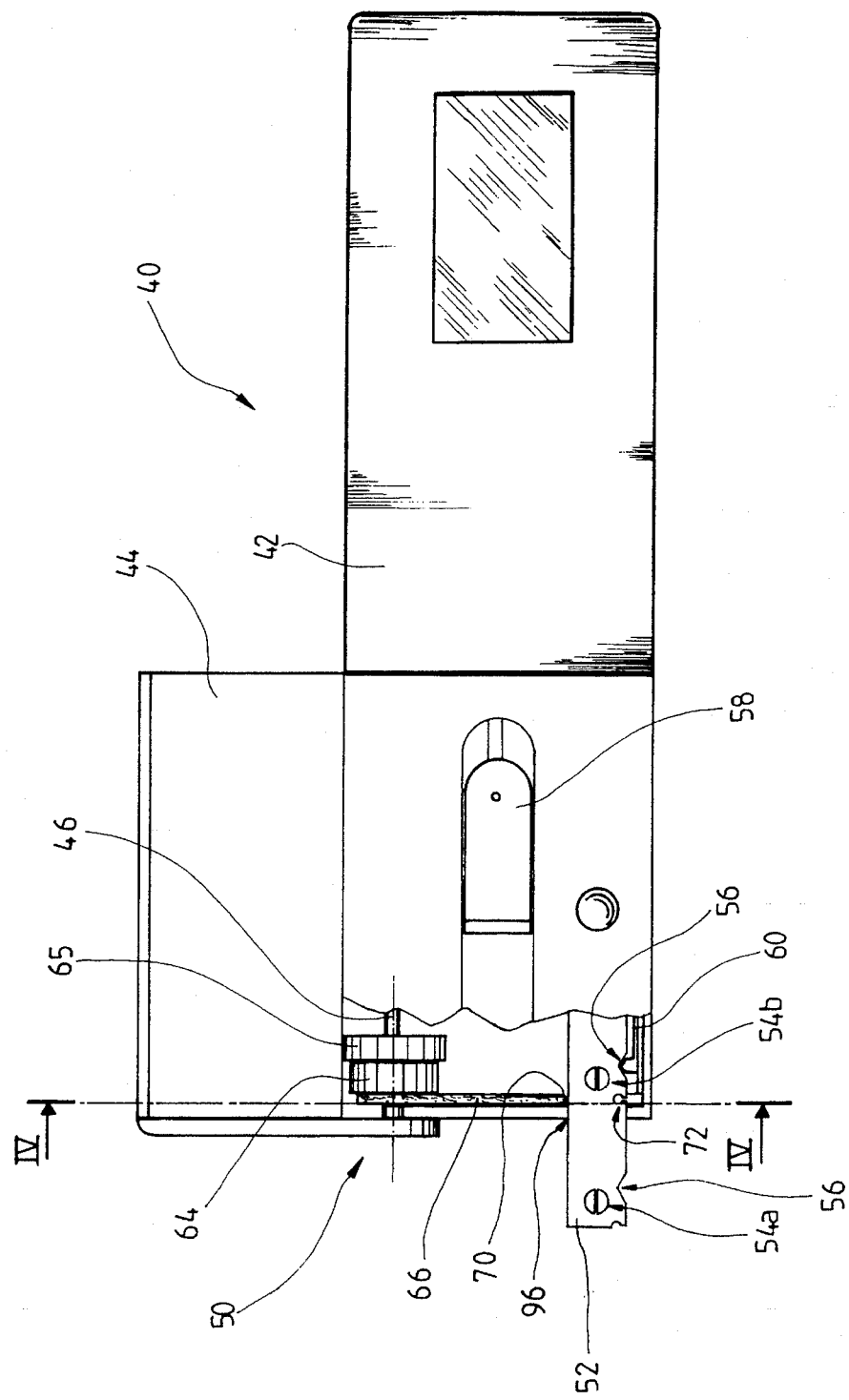
FIG. 3 is a top view partially broken away of a measurement arrangement according to the invention, such figure showing a cutting arrangement associated with a cover shown in an initial cutting position.

On FIG. 3, the measurement arrangement designated by the general reference 40 comprises a case 42 and a cover 44 adapted to undergo a rotation around a first rotation axle 46. The measurement arrangement 40 also includes a cutting arrangement 50 serving to cut off a multiple zone removable sensor 52 associated with the measurement arrangement 40.

The multiple zone removable sensor 52 includes a plurality of active zones 54a, 54b. Each of the active zones 54a, 54b of the multiple zone removable sensor 52 is for a single use, that is to say, that it serves to effect a single measurement of a substance to be analyzed.

After having utilized an active zone in order to effect a measurement, specifically a measurement of the electrochemical type, there is a provision to cut off the multiple zone removable sensor 52 with the help of the cutting arrangement 50 in order to separate the portion of such sensor 52 including such used active zone from the remainder of the latter.

After having cut off the multiple zone removable sensor, it is possible to displace such sensor with the help of an advancing arrangement (not shown) comprising in particular a push-piece 58 in order to permit a new blank active zone 54a to be located outside the case 42. The arrangement of the sensor 52 and the advancing arrangement which is associated therewith permit a single active zone to be located outside the case 42, such active zone being then intended to receive the substance to be analyzed during a subsequent measurement.

The multiple zone removable sensor 52 can be maintained in a plurality of different positions with the help of positioning notches 56 cooperating with a positioning spring 60.

The cutting arrangement 50 includes a lever formed by a cover 44 fixed to a disc or cylinder 64 the central axis of which coincides with the first rotation axle 46. Cylinder 64 can be formed together with cover 44 or be secured to a piece 65 itself making up part of cover 44 as shown on FIGS. 3 to 5. The cutting arrangement comprises additionally a crank 66 coupled at a first end to the cylinder 64 in an off-centered manner, such crank 66 being adapted to undergo rotation around a second axle 68 fixed to the cover 44. Crank 66 is coupled rigidly to a blade 70 serving to cut off the multiple zone removable sensor 52.

It will be noted that, advantageously, the multiple zone detachable sensor 52 includes a plurality of openings 72 (a single opening being shown on FIG. 3), such openings 72 being arranged along the sensor 52. Each of the openings 72 is arranged in a manner to be traversed by blade 70 during cutting of the sensor 52 retained in one of the said different positions provided for sensor 52 in the measurement arrangement 40. Such opening 72 serves to absorb strain energy resulting from the pressure exerted by the blade 70 on the material forming the sensor 52 during cutting of the latter.

Figure 4:
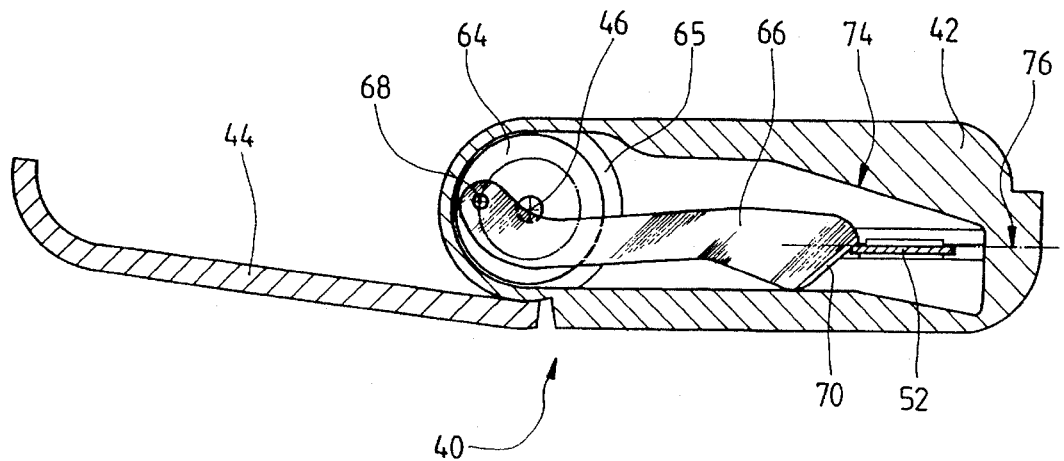
FIG. 4 is a cross-section of FIG. 3 taken along section line IV—IV.

On FIGS. 3 and 4, cover 44 and the blade 70 are shown in an initial cutting position.

Figure 5:
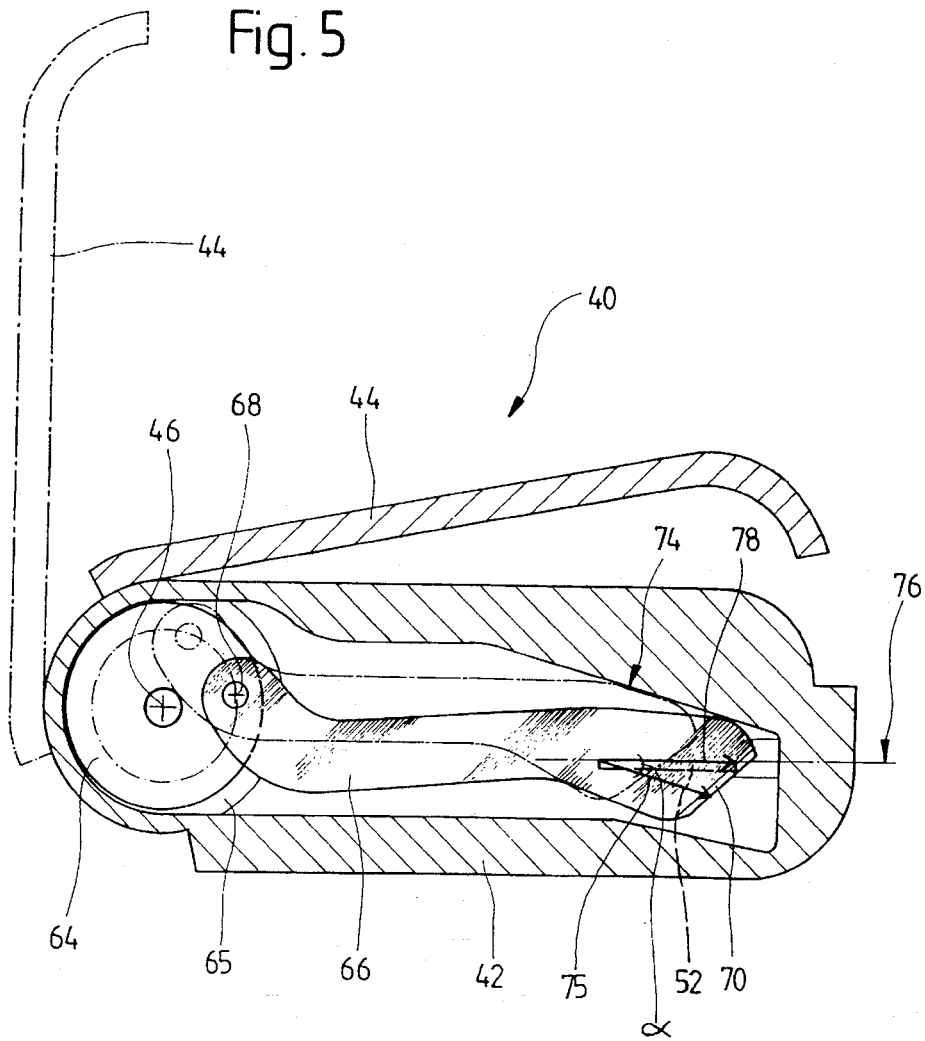
FIG. 5 is a cross-sectional view similar to FIG. 4 which shows in broken lines the cover in an intermediate cutting position, and in full lines, such cover in a final cutting position.

On FIG. 5 cover 44 and blade 70 are shown in broken outline in an intermediate cutting position and in full line in a final cutting position. When cover 44 is actuated between said initial cutting position and said final cutting position, blade 70 traverses a cutting path defined by a guide 74 arranged within case 42.

It will be noted that the multiple zone removable sensor 52 is of elongated form and flat, defining a general plane 76 of such sensor 52. During the actuation of cover 44 between the initial cutting position and the final cutting position, sensor 52 is cut off by blade 70 according to a cutting direction 78.

Guide 74 is arranged in a manner such that blade 70 traverses a path between its initial cutting position and its final cutting position defining an advancing direction 75 of such blade 70 which is angularly separated by an angle α relative to the cutting direction 78. Through this fact, the penetration of the blade into the material is facilitated. Effectively, during cut off of the sensor 52, blade 70 undergoes a motion perpendicular to the general plane 76 of the multiple zone removable sensor 52. There also results from this fact uniform wearing of blade 70 and consequently a lesser wear than in the case in which the contact zone between blade 70 and sensor 52 remains identical throughout the cutting of such sensor 52.

It will further be noted that the first and second rotation axles 46 and 68 are parallel to one another and that the distance separating such two axles is less than the length of the lever formed by cover 44. The design of the cutting arrangement 50 transforms a circular motion of cover 44 actuated by a user into a substantially rectilinear motion of blade 70. Such design exhibits the advantage of transforming a uniform circular motion, that is to say, having a constant angular velocity, into a rectilinear motion of blade 70 the speed of which varies in a sinusoidal manner between said initial cutting position and said final cutting position. From this fact the speed of blade 70 during the engagement with sensor 52 and at the end of the cutting of sensor 52 is very small.

The form of crank 66 is particularly well adapted to a measurement arrangement exhibiting a relatively low height. However, when cover 44 is actuated between said initial cutting position and said final cutting position, crank 66 intercepts the first rotational axle 46. Because of this, in this special embodiment, axle 46 coupled to cylinder 64 on which is secured axle 68 also serving for retention of crank 66 must not project beyond cylinder 64 into the region destined for crank 66.

Figure 6:
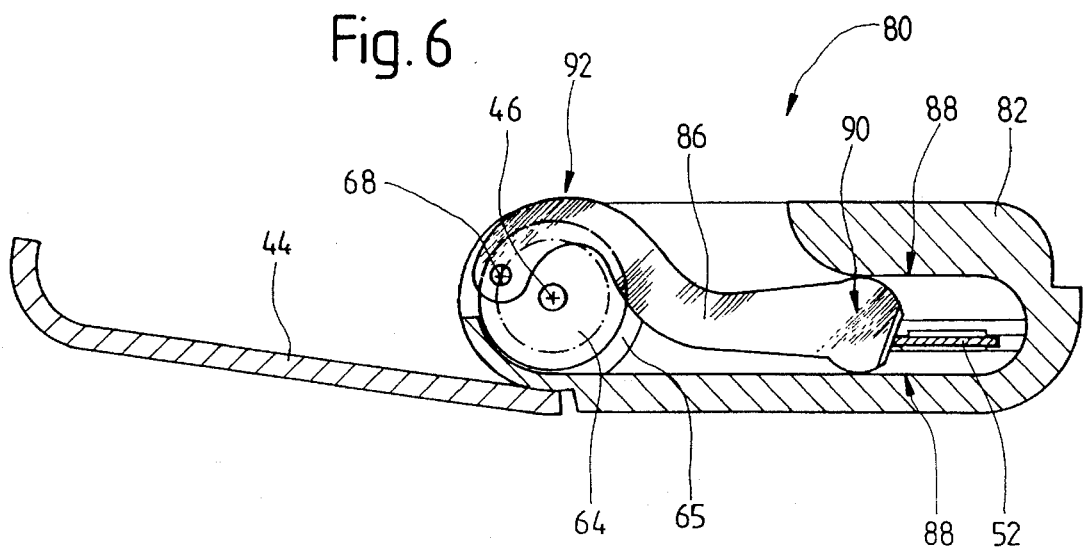
FIGS. 6 and 7 are respectively similar to FIGS. 4 and 5, but show a variant embodiment of the cutting arrangement described in FIGS. 3 to 5.
Figure 7:
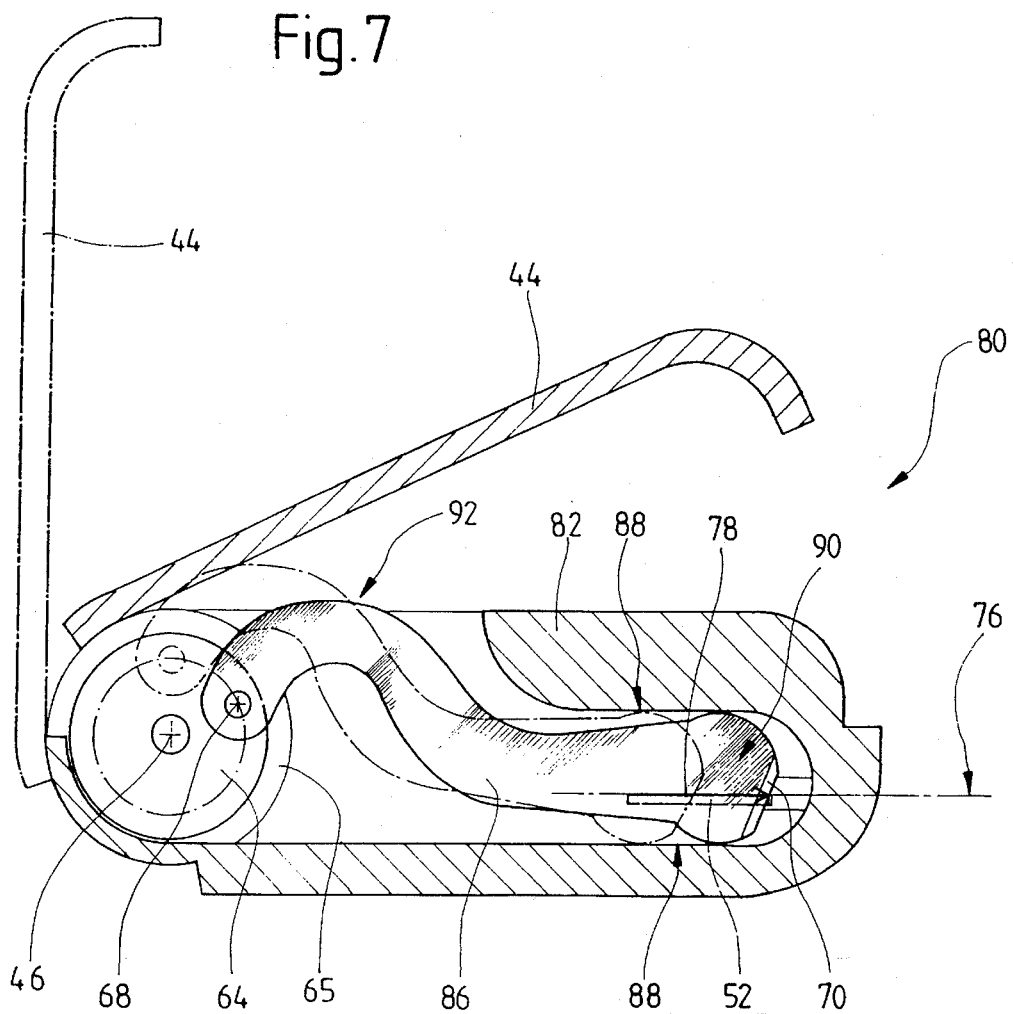

On FIGS. 6 and 7 is shown a variant of the embodiment described with the help of FIGS. 3 to 5.

In this variant, the measurement arrangement 80 also includes a case 82 and a cover 44 serving as actuating lever for a crank 86 rigidly fixed to a blade 70. The actuating system, by means of cover 44, of blade 70 fixed to crank 86 is identical to the system described hereinbefore.

This variant differs basically from the embodiment described hereinbefore by the form of crank 86 and by the design of the guide 88 defining a cutting path for blade 70.

Guide 88 defines a rectilinear path for blade 70 between an initial cutting position shown on FIG. 6 and a final cutting position shown in full line on FIG. 7. On such FIG. 7 is also shown an intermediate cutting position in broken outline.

Although the path imposed by guide 88 on head 90 of the crank 86 bearing blade 70 is rectilinear and parallel to the cutting direction 78, blade 70 undergoes a slight vertical motion, that is to say, perpendicular to the general plane 76 of sensor 52 when cover 44 and blade 70 are user actuated between said initial cutting position and said final cutting position. Such slight vertical movement results from a slight rotation of head 90 of crank 86 which exhibits a circular form.

Crank 86 in this variant exhibits an elbow 92. Such elbow 92 is formed in a manner such that the crank 86 never intercepts the first axle 46 around which cover 44 is adapted to undergo a rotation. In this latter case, axle 46 can readily project outside cylinder 64 on the side of crank 86. In particular, such axle 46 can traverse entirely the region provided for crank 86 in a manner to be secured to cover 44 from the other side of cylinder 64 relative to crank 86.

It will be noted that cover 44 is adapted to undergo a rotation through an angle of about 180° in the embodiment and in the variant of such embodiment described hereinbefore. However, it is easily possible to provide an angular path through a different angle for cover 44. It will be also noted that cover 44 can also serve to protect orifice 96 shown on FIG. 3 formed in case 42 or 82 for the introduction of sensor 52 into the interior of such case.

Finally, it will be noted that it is possible to conceive embodiments of the invention in which the blade 70 is adapted to undergo a movement relative to crank 66, 86 to which is mechanically coupled.

What we claim is:

1. A measurement arrangement for use with a multiple zone removable sensor disposed at least partially within the measurement arrangement, said measurement arrangement including means for applying an electrical signal to said sensor to produce a measurement signal and a cutting device for cutting a zone from said multiple zone removable sensor after the zone has been brought into contact with a sample to effect a measurement, said cutting comprising:

a lever fixed to a first axle pivotable about a first axis;

a second axle having a second axis, said second axle being movable about said first axle;

a crank having a first end coupled to said second axle and freely pivotable about said second axis, said crank having a second end to which a blade is mechanically coupled;

means for mechanically coupling said first axle to said second axle whereby pivoting of said lever causes movement of said crank; and, a guide for guiding said second end of said crank along a path so that said second end of said crank moves toward and away from a multiple zone removable sensor as said lever is pivoted in a first and a second direction, respectively, whereby said blade cuts a multiple zone removable sensor disposed in said path and said blade is then retracted.

2. A measurement arrangement as set forth in claim 1, said second axle being parallel to, and spaced a distance from, said first axle, said lever having a dimension greater than the distance between said first axle and said second axle in a plane perpendicular to said first axle and said second axle.

3. A measurement arrangement as set forth in claim 1, wherein said blade is rigidly coupled to said crank.

4. A measurement arrangement as set forth in claim 1, wherein said guide defines a substantially rectilinear guide path.

5. A measurement arrangement as set forth in claim 1, for use with a multiple zone removable sensor of elongated form and substantially flat defining a generally plane for such multiple zone removable sensor and a cutting direction for said blade in such general plane, wherein said guide is arranged in a manner such that, when said multiple zone removable sensor is placed in said measurement arrangement, said path defined by said guide between an initial cutting position of the blade and a final cutting position of said blade, corresponding respectively to said initial cutting position and final cutting position of said lever, determines a travel direction for said blade angularly offset relative to said cutting direction.

6. A measurement arrangement as set forth in claim 1, wherein said crank exhibits an elbow arranged in a manner such that said crank never intersects said first axle.

7. A measurement arrangement as set forth in claim 1, wherein said lever may pivot through an angle substantially equal to 180°.

8. A measurement arrangement as set forth in claim 1, wherein said measurement arrangement and said multiple zone removable sensor associated therewith are arranged to measure the proportion of glucose in blood.

9. A measurement arrangement as set forth in claim 1, wherein said lever comprises a cover serving in addition to protect a push-piece serving for the advancing of said multiple zone removable sensor.

10. A measurement arrangement as set forth in claim 9, wherein said cover serves to close an orifice serving for the introduction of the multiple zone removable sensor into the interior of said measurement arrangement.

11. A measurement arrangement for use with a multiple zone and generally planar removable sensor that may be disposed in a first plane and at least partially within the measurement arrangement, the measurement arrangement including means for applying an electrical signal to said sensor to produce a measurement signal and a cutting device for cutting a zone from said multiple zone removable sensor after the zone has been brought into contact with a sample to effect a measurement, said cutting comprising:

a lever fixed to a first axle so as to pivot about a first axis;

a second axle having a second axis, said second axle being movable about said first axle;

a crank having a first end coupled to said second axle, said crank being freely pivotable about said second axis;

means for mechanically coupling said first axle to said second axle;

a blade mechanically coupled to a second end of said crank; and, a guide for guiding said second end of said crank along a guide path whereby said blade moves in a cutting direction parallel to the first plane in which a sensor is disposed to thereby cut a sensor as said lever is pivoted about said first axis.

12. A measurement arrangement as set forth in claim 11, said second axle being parallel to, and spaced a distance from, said first axle, said lever having a dimension greater than the distance between said first axle and said second axle in a plane perpendicular to said first axle and said second axle.

13. A measurement arrangement as set forth in claim 11, wherein said guide defines a substantially rectilinear guide path.

14. A measurement arrangement as set forth in claim 11, wherein said crank exhibits an elbow arranged in a manner such that said crank never intersects said first axle.

15. A measurement arrangement as set forth in claim 11, wherein said lever comprises a cover serving in addition to protect a push-piece serving for the advancing of said multiple zone removable sensor.

16. A measurement arrangement as set forth in claim 11, wherein said cover serves to close an orifice serving for the introduction of the multiple zone removable sensor into the interior of said measurement arrangement.

17. A measurement arrangement as claimed in claim 11 wherein said guide comprises means confining said second end of said crank to a path of movement in a direction forming an acute angle with respect to the first plane.

18. A measurement arrangement as claimed in claim 17 wherein said blade is disposed at an angle to said cutting direction and in a second plane normal to said first plane.

19. A measurement arrangement as claimed in claim 11 wherein said guide comprises means confining said second end of said crank to a path of movement in a direction forming an acute angle with respect to the first plane.

20. A measurement arrangement as claimed in claim 19 wherein said blade is disposed at an angle to said cutting direction and in a second plane normal to said first plane.

* * * * *